United States Patent
Mirsky

[11] 3,941,660
[45] Mar. 2, 1976

[54] METHOD AND APPARATUS FOR DETECTING MICRO-ORGANISMS

[76] Inventor: Jeffrey Mirsky, 379 Morris Ave., Mountain Lakes, N.J. 07646

[22] Filed: Jan. 20, 1975

[21] Appl. No.: 542,259

[52] U.S. Cl. .............. 195/103.7; 195/127; 195/139
[51] Int. Cl.² .......................................... C12K 1/04
[58] Field of Search ............ 195/103.5 R, 127, 139, 195/103.7

[56] References Cited
UNITED STATES PATENTS

| | | | |
|---|---|---|---|
| 2,914,447 | 11/1959 | Levin | 195/103.7 |
| 3,844,894 | 10/1974 | Kronick et al. | 195/103.5 R |
| 3,858,045 | 12/1974 | Waters | 195/103.7 |

Primary Examiner—A. Louis Monacell
Assistant Examiner—Robert J. Warden
Attorney, Agent, or Firm—L. H. Birnbaum

[57] ABSTRACT

A method and apparatus is described for determining the presence and quantity of micro-organisms, such as bacteria, fungue and yeast, in a given sample. The apparatus includes two sealed containers, a portion of which may be penetrated by a sharp instrument, as for example, glass vials with flexible septum tops. One container includes a radioactive nutrient medium which is capable of s supporting the life process of the micro-organism whose presence is being tested. The second container includes a liquid scintillation solution which absorbs the product of metabolism of the organisms. The sample is introduced into the first sealed container, for example, by means of a standard syringe. Any micro-organisms present will consume the radioactive nutrient and as a result produce radioactive waste. Means are then applied to penetrate the containers and allow the flow of the radioactive metabolic product from the first container to the second container while preventing any contamination from the ambient. The liquid scintillation solution will emit light in proportion to the amount of the product of metabolism collected from the first container. This light may be detected by standard liquid scintillation counters, thus providing a qualitative and quantitative measure of the micro-organism in the tested sample.

26 Claims, 2 Drawing Figures

METHOD AND APPARATUS FOR DETECTING MICRO-ORGANISMS

BACKGROUND OF THE INVENTION

This invention relates to a method and apparatus for detecting the presence of micro-organisms.

The need presently exists, in a great variety of applications, for detecting the presence of micro-organisms, especially bacteria of various types. In clinical medicine and medical research, it is frequently necessary to determine the bacteria count of blood, urine or tissue cultures. In the food and drug industry, it is essential that lots be tested for purity to insure safe consumption of the product.

Various methods have been proposed for such testing. For example, in laboratory testing it has been suggested that the sample be mixed with a radioactive nutrient medium in a flask and a cup containing a $CO_2$ absorbing material be held above the medium to collect gas emitted by any bacteria (Warburg apparatus). The cup is then removed from the flask and the absorbing material mixed with a liquid scintillation solution. The light emitted from the solution as a result of the $CO_2$ contained in the material is then measured by a scintillation counter. It will be realized that this process is fairly cumbersome and would not be entirely suitable for testing on a large scale. In addition, exposing the sample and the $CO_2$ absorbing material to the ambient could lead to contamination. Furthermore, only a small amount of $CO_2$ can be absorbed by that method and sensitivity is reduced. Other methods have been proposed utilizing the concept of measuring the $CO_2$ emitted by micro-organisms during a life-support process, whether for measuring directly the sterility of a sample or for the distinctly different objective of determining the efficacy of a sterilization process by including a special chamber in the sterilizing atmosphere (see for example, U.S. Pat. No. 3,657,073 and U.S. Pat. No. 3,313,712). Presently available methods usually suffer from one or more of the problems of unreliability, contamination, ineffectiveness of separating nutrient medium from detection means, or excessively costly or complex equipment. It is therefore a primary object of the present invention to provide a reliable apparatus and method for detecting micro-organisms with a minimum number of processing steps and utilizing inexpensive, disposable apparatus to permit testing on a large scale.

SUMMARY OF THE INVENTION

In accordance with the invention, apparatus is provided which includes two sealed containers which may be penetrated without exposing the contents to the environment, as for example, glass vials with flexible septum tops. A first container includes a radioactive nutrient medium which is utilized in the life process of the organism to be tested, and the second container includes a liquid scintillation solution which can indicate the presence of radioactive metabolic products by emitting light in response thereto. The sample to be tested is introduced into the first container by penetrating with a sharp instrument such as a standard syringe. Means are provided in the apparatus for coupling together the two containers such that the metabolic products produced in the first will be introduced into the second. The light produced by the scintillation solution can then be measured by a standard scintillation counter and the presence of micro-organisms therefore determined.

BRIEF DESCRIPTION OF THE DRAWING

These and other features of the invention will be delineated in detail in the description to follow. In the drawing.

DETAILED DESCRIPTION OF THE INVENTION

Figure 1:
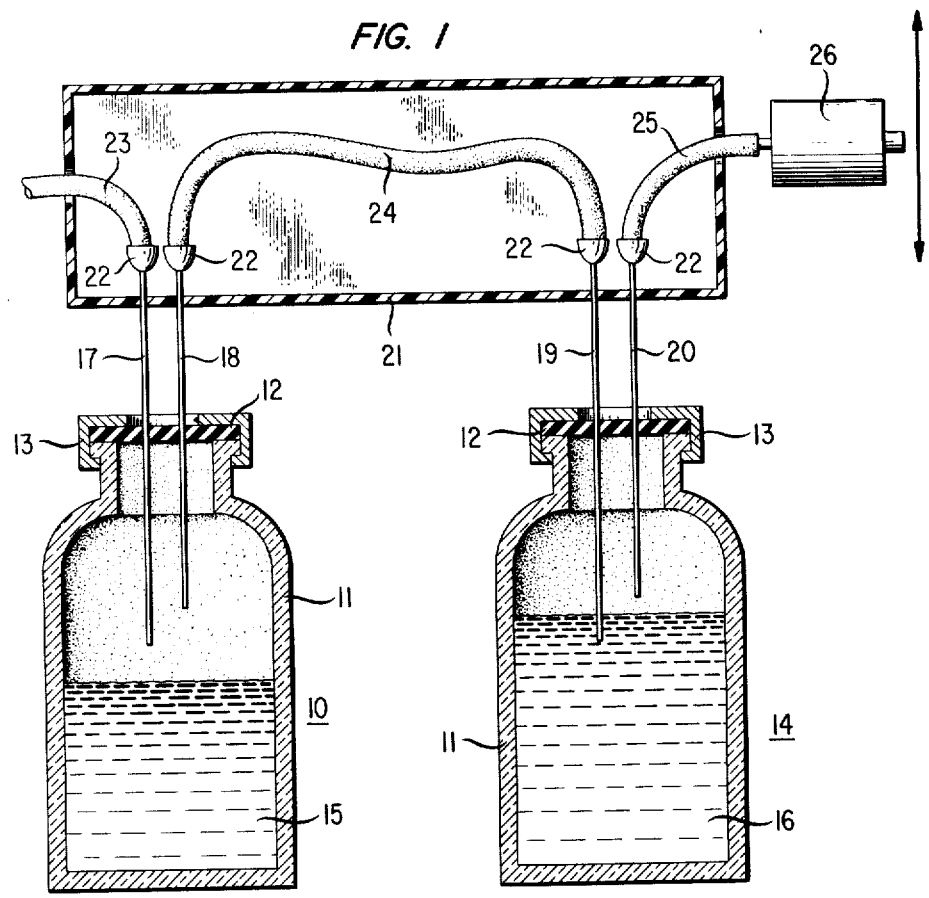
FIG. 1 is a cross-sectional view, partly schematic, of apparatus for detecting the presence of micro-organisms in accordance with one embodiment of the invention.

The method, as well as the apparatus, of the invention can best be described in relation to FIG. 1. A first sealed container, 10, comprises a glass vial 11, with a flexible membrane 12, tightly secured to the top by cap 13. The flexible cover can be any suitable material which is resilient enough to be penetrated by a sharp instrument without exposing the contents of the vial to the ambient and which is inert to the contents of the container. A material found particularly suitable is a teflon-lined rubber membrane, but any of a number of other materials may be used. The container itself may also be made from other materials such as plastic. A second sealed container 14, is also provided which in the above respects may be identical to the first container.

Within the first container 10, there is a liquid nutrient medium 15, which is radioactive. The particular medium chosen will depend on the type of micro-organism which is being tested for. In general, it is known in the art what medium will support the life processes of a particular organism. For example, for the detection of E. coli bacteria, a suitable medium would be fluid thioglycollate medium along with a radioactive material comprising L-Cystine ($^{14}C$). Provided within the second vial 14, is a liquid scintillation solution 16. The solution is one which will absorb the metabolic products of the micro-organisms, intersperse the products homogeneously throughout the solution and emit light in response thereto. In this embodiment, radioactive carbon dioxide will be produced by the micro-organisms in vial 10. A particularly useful material for detecting $CO_2$ has been found to comprise: approximately 500 ml/liter of a solvent of toluene or xylene, approximately 5 gms/liter of a primary phosphor such as 2,5-diphenloxazole (PPO), approximately 200 mg/liter of a secondary phosphor such as 2,2'-p-phenylenebis (5-phenyloxazole) (POPOP), approximately 300 ml/liter of phenethylamine as a trapping agent, and approximately 200 ml/liter of a secondary solubility agent such as methanol. Other solutions capable of performing the functions necessary in the present invention may be either known in the art or devised, and such solutions may be utilized in place of the particular example described here. It will also be clear that the proportions given here are illustrative and may be varied.

The apparatus further includes a first pair of needles 17 and 18, which are capable of penetrating the top of the first vial without exposing the contents to the ambient, and a second pair of needles 19 and 20, which are likewise capable of penetrating the top of the second vial. These needles are secured within a suitable holder 21, which is cut away for purposes of illustration in FIG. 1. The holder may comprise, for example, aluminum. Each needle is coupled by means of fittings, 22, such as luer fittings, to an opening in one of three pieces of tubing provided in the holder. The tubes may be made of a material such as neoprene. As shown, needle 17 is coupled to tubing 23 which extends outside the holder, needles 18 and 19 to opposing ends of tube 24, and needle 20 to one opening of tube 25 which also extends outside the holder and is coupled to a receptacle 26. The holder is capable of moving in a vertical direction in the Figure so that the needles may be inserted in and withdrawn from the vials, the holder being in the lower position in FIG. 1. Any suitable mechanical means (not shown) may be provided for this purpose. For example, the holder may be operated by a lever as in a standard drill press or by a rotating knob by utilizing a worm screw. The precise means employed for this purpose is not significant in the context of the invention.

In accordance with this embodiment of the method of the invention, the holder is initially in its upper position so that the needles have not penetrated the vial tops. The sample to be tested is introduced into container 10, by penetrating the top with a standard syringe (not shown). Any bacteria present in the test sample will feed on the nutrient medium 15 in container 10 and as a result give off radioactive $CO_2$. A sufficient period of time should be allowed to permit the bacteria to grow (approximately 15 minutes). The containers are then put in place and the holder 21 is lowered to the position shown in FIG. 1 so that the needles penetrate into the appropriate container. Advantageously, tube 23 is coupled to a source of inert gas (not shown), such as nitrogen so that the gas is introduced into container 10 through needle 17. It will be noted that needle 17 lies above the liquid medium 15. The inert gas flushes out any radioactive $CO_2$ through needle 18. The radioactive $CO_2$ therefore flows through tube 24 and needle 19 into container 14. In particular, since needle 19 preferably extends into the solution 16, the $CO_2$ is introduced directly into the liquid. The solution 16, will absorb the $CO_2$ present and emit light in proportion thereto. Thus, after a short period of time (of the order of a few seconds), the holder is raised and the container 14 removed. The light emanating from container 14 can be measured by placing the container in a standard liquid scintillation counter (not shown). The measure of light therefore provides an accurate measure of any bacteria present in the tested sample. If any excess $CO_2$ is produced, it will flow through needle 20 and tube 25 into receptacle 26 which acts as a $CO_2$ trap. This receptacle may be removed when full and replaced.

It will be seen that many advantages accrue from the method and apparatus of the invention. The system is completely closed to the environment thus preventing any contamination which would result in errors in measurement. The process is easily performed on a large scale. The vials used are disposable, while the holder and its associated tubes and needles may be used repeatedly. The apparatus is also inexpensive. The only complex equipment required in the entire operation is the liquid scintillation counter. However, counters are usually standard equipment for other applications in research laboratories and hospitals and so no extraordinary expense would be required for the present application.

An additional advantage of the present invention over most prior art methods is the capability of a quantitative as well as qualitative measurement. The number of counts produced by the scintillation counter will be proportional to the number of light bursts in the scintillation solution, which in turn will be directly proportional to the amount of $CO_2$ produced. Thus, the number of counts can be correlated to the number of bacteria present in the sample.

Figure 2:
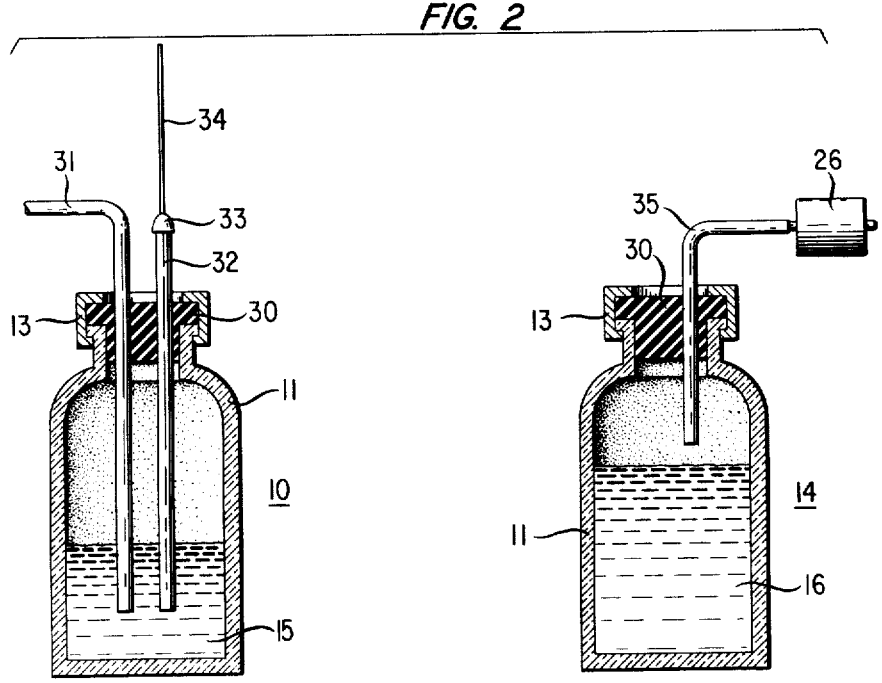
FIG. 2 is a cross-sectional view of apparatus for detecting the presence of micro-organisms in accordance with a further embodiment of the invention.

A second embodiment of the invention is shown in FIG. 2, with elements of the apparatus corresponding to those of FIG. 1 similarly numbered. As in the previous example, two sealed containers 10 and 14, are provided which include, respectivley, a radioactive nutrient medium 15 and a liquid scintillation solution 16. In this case, however, the containers are shown as sealed by rubber stoppers 30. Other means may be employed to close off the containers including the membrane of the previous embodiment, as long as the material is resilient and inert to the contents of the container. Container 10 is provided with a pair of tubes 31 and 32, which extend from the environment through the rubber stopper into the liquid medium as shown. The tubes may, for example, be made of glass or metal. Attached to one end of tube 32 by means of fitting 33 is a needle 34. Caps (not shown) may be provided at the end of tube 31 and needle 34 to prevent contamination of the medium prior to use. Tube 35 extends through the stopper of container 14 and terminates in the space above the liquid scintillation solution 16. The end of tube 35 outside the container may be coupled to receptacle 26.

In accordance with this embodiment, the test sample is introduced by piercing the stopper with a standard syringe (not shown) as in the previous example. After giving the micro-organisms a chance to grow (a period of approximately 15 minutes), the container 10 is turned upside down and needle 34 is inserted through stopper 30 of container 14. The length of needle 34 is chosen so that when inserted it can extend into the liquid 16. The lengths of tubes 31 and 32 are also chosen so that when container 10 is inverted, the ends of the tubes lie in the space above liquid 15. Tube 31 can then be coupled to a source of inert gas (not shown) such as nitrogen in order to flush out of container 10 any radioactive $CO_2$ produced by the micro-organisms. The $CO_2$ thereby flows through tube 32 and needle 34 into liquid 16. Again, the two containers need be coupled together for only a few seconds. Any excess $CO_2$ will flow through tube 35 into receptacle 26 which acts as a $CO_2$ trap, as in the previous embodiment.

The vials are then decoupled and container 14 in placed in a liquid scintillation counter as before to measure the light produced by liquid 16 in response to the $CO_2$ absorbed therein. It will seen that this embodiment affords the same advantages as the previous embodiment, with the added feature of not requiring any special apparatus external to the vials for allowing the $CO_2$ to flow from one vial to the other.

While the above-described embodiments have utilized the detection of radioactive carbon dioxide produced by micro-organisms, it should be clear that other products of metabolism may be measured with some modifications in the contents of the two vials. For example, it is possible to detect radioactive water produced by the micro-organisms, if the nutrient medium in the first vial (10) includes tritiated cystine as the radioactive element and the second vial (14) includes a substance for absorbing the water and emitting light, such as a solvent of p-dioxane, approximately 5 gm/liter of PPO and approximately 200 mg/liter of POPOP. Similarly, radioactive $SO_2$ may be produced and detected if the nutrient medium includes L-Cystine ($S^{35}$) and the solution in vial 14 comprises one which will absorb $SO_2$ and emit light such as approximately 500 ml/liter of a solvent such as toluene, approximately 5 gm/liter of PPO, approximately 200 mg/liter of POPOP and approximately 200 mg/liter of methanol as a trapping agent. Again, these proportions are illustrative.

Various additional modifications will become apparent to those skilled in the art. All such variations which basically rely on the teachings through which the invention has advanced the art are properly considered within the spirit and scope of the invention.

What is claimed is:

1. Apparatus for detecting micro-organisms in a sample comprising:
   a first sealed container into which the sample may be introduced including therein a radioactive nutrient medium which is capable of supporting the life process of the micro-organisms to be detected;
   a second sealed container including therein a solution which is capable of absorbing the radioactive metabolic product of the micro-organisms in said sample and emitting light in response thereto; and
   means for coupling together the first and second containers so that the radioactive metabolic product produced by the micro-organisms of the sample in the first container may be introduced into said second container without contamination of the contents of said containers by the environment and without physical contact of the medium with any portion of the second container.

2. The apparatus according to claim 1 wherein each of said containers includes an opening covered by a resilient material which material may be penetrated by said means without exposing the contents to the environment.

3. The apparatus according to claim 1 wherein the means comprises first and second needles coupled to opposing ends of a first conduit and secured in spaced relation by a movable holder such that each of said needles may be inserted into one of said containers to allow the radioactive metabolic product to flow from the first to the second container and said needles may then be withdrawn without contamination of the contents by the environment.

4. The apparatus according to claim 3 further comprising
   a third needle secured by said holder adjacent to said first needle and coupled to a second conduit, said third needle being in position to penetrate said first container along with said first needle and said second conduit extending outside said holder.

5. The apparatus according to claim 4 further comprising
   a fourth needle secured by said holder adjacent to said second needle and coupled to a third conduit extending outside said holder, said fourth needle being positioned so as to penetrate said second container along with said second needle.

6. The apparatus according to claim 1 wherein each of said containers includes an opening therein sealed by a resilient material and said means for coupling the containers comprises a tube extending through said material of said first container one end of which extends within the container and the other end of which extends outside said container and further comprising a needle coupled to the end of the tube extending outside the container which needle is capable of penetrating the resilient material of said second container without contamination of the contents by the environment.

7. The apparatus according to claim 6 further comprising a second tube extending through the resilient material of the first container, one end of which extends into the container and the other end of which extends outside the container and which may be coupled to a source of gas for flushing the radioactive metabolic product out of said container, and a third tube extending through the resilient material of said second container one end of which extends into the second container in the space above said solution and the other end of which extends outside the container and may be coupled to a receptacle for collecting the excess metabolic product introduced into said second container.

8. The apparatus according to claim 1 wherein the solution in said second container comprises a solvent selected from the group consisting of toluene and xylene, 2,5-diphenyloxazole, 2,2'-p-phenylenebis (5-phenyloxazole), phenethylamine, and methanol.

9. The apparatus according to claim 1 wherein the nutrient medium comprises fluid thioglycollate and L-Cystine ($^{14}C$).

10. Apparatus for detecting micro-organisms in a sample comprising:
    a first sealed container into which the sample may be introduced defining a volume including therein a radioactive liquid nutrient medium which is capable of supporting the life process of the micro-organism to be detected;
    a second sealed container defining a volume therein including a solution which is capable of absorbing radioactive carbon dioxide produced by the micro-organisms in said sample and emitting light in response thereto, each of said containers comprising a rigid enclosure including an opening therein covered by a resilient material which may be penetrated by sharp instruments without exposing the contents of said containers to the environment; and
    means for coupling together the volumes of the containers comprising first and second needles coupled to opposing ends of a first conduit and secured in spaced relation by a movable holder such that each of said needles may be inserted through the resilient material of a respective one of said containers to allow radioactive $CO_2$ to flow from the first to the second container and said needles can then be withdrawn without exposing the contents of the containers to the environment.

11. Apparatus according to claim 10 further comprising a third needle secured by said holder adjacent to said first needle and coupled to a second conduit which may be coupled to a source of inert gas, said third needle being in position to penetrate said first container along with said first needle.

12. Apparatus according to claim 11 further comprising a fourth needle secured by said holder adjacent to said second needle and coupled to a third conduit which may be coupled to a receptacle for receiving excess radioactive carbon dioxide introduced into said second container, said fourth needle being positioned so as to penetrate said second container along with said second needle.

13. Apparatus according to claim 10 wherein the solution contained in said second container comprises a solvent selected from the group consisting of toluene and xylene, 2,5-diphenyloxazole, 2,2'-p-phenylenebis (5-phenyloxazole), phenethylamine, and methanol.

14. Apparatus according to claim 10 wherein the liquid nutrient medium comprises fluid thioglycollate and L-Cystine ($^{14}C$).

15. Apparatus for detecting micro-organisms in a sample comprising:
- a first sealed container into which the sample may be introduced defining a volume therein including a radioactive liquid nutrient medium which is capable of supporting the life process of the micro-organisms to be detected;
- a second sealed container defining a volume therein including a solution which is capable of absorbing radioactive carbon dioxide produced by the micro-organisms in said sample and emitting light in response thereto, each of said containers comprising a rigid enclosure including an opening therein covered by a resilient material which may be penetrated by sharp instruments without exposing the contents of said containers to the environment; and
- means for coupling together the volumes of the containers comprising a first conduit extending through the resilient material of the first container one end of which extends within the container and the other end of which extends outside the container and further comprising a needle coupled to the end of the conduit extending outside the container, which needle is capable of penetrating the resilient material of the second container and extending into the solution of the second container without contamination of the contents by the environment.

16. Apparatus according to claim 15 further comprising a second conduit extending through the resilient material of the first container one end of which extends into the container and the other end of which extends outside the container and which may be coupled to a source of gas for flushing the radioactive carbon dioxide out of said container.

17. Apparatus according to claim 15 further comprising a third conduit extending through the resilient material of said second container, one end of which extends into the second container above said solution and the other end of which extends outside the container and may be coupled to a receptacle for collecting excess carbon dioxide introduced into said second container.

18. Apparatus according to claim 15 wherein the solution in said second container comprises a solvent selected from the group consisting of toluene and xylene, 2,5-diphenyloxazole, 2,2'-p-phenylenebis (5-phenyloxazole), phenethylamine, and methanol.

19. Apparatus according to claim 15 wherein the liquid nutrient medium comprises fluid thioglycollate and L-Cystine ($^{14}C$).

20. A method of detecting micro-organisms in a sample comprising the steps of:
- introducing said sample into a sealed container defining a volume which includes therein a radioactive nutrient medium which is capable of supporting the life process of the micro-organisms to be detected;
- coupling together the volume of said first container with the volume defined by a second sealed container which includes therein a solution capable of absorbing the radioactive metabolic product of the said sample and emitting light in response thereto, so that the metabolic product produced in said first container is introduced into said second container, said coupling being done without exposure of the contents of the container to the environment;
- de-coupling the volumes of the two containers; and
- measuring the light emitted by the solution in said second container in response to the metabolic product of the micro-organisms of the sample.

21. The method according to claim 20 wherein the light is measured by a liquid scintillation counter.

22. The method according to claim 20 wherein the nutrient medium comprises fluid thioglycollate and L-Cystine ($^{14}C$).

23. The method according to claim 20 wherein the solution within the second container comprises a solvent selected from the group consisting of toluene and xylene, 2,5-diphenyloxazole, 2,2'-p-phenylenebis (5-phenyloxazole), phenethylamine, and methanol.

24. The method according to claim 20 wherein the volumes of the containers are coupled together by inserting first and second needles respectively, through said first and second containers, said needles being coupled to opposing ends of a conduit which is capable of transmitting the radioactive metabolic product therethrough.

25. The method according to claim 20 wherein the volumes of the containers are coupled together by inserting a needle through said second container which needle is coupled to one end of a conduit secured to said first container where the other end of said conduit lies within the volume of said first container.

26. The method according to claim 20 wherein the radioactive metabolic product of the micro-organisms is flushed out of said first container by introducing an inert gas into the volume of the first container.

* * * * *